Figure 1:
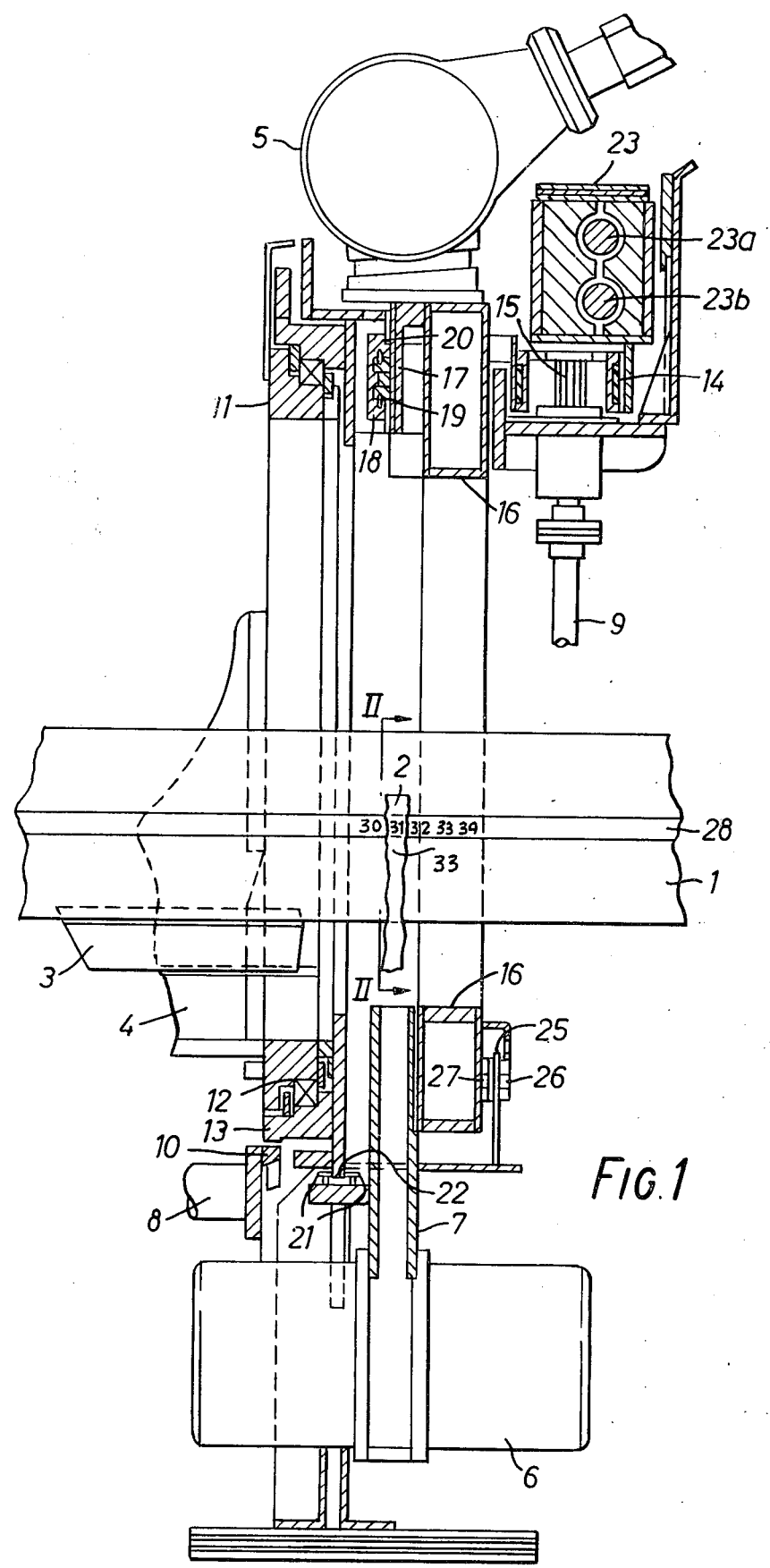

United States Patent [19]
Oldendorf

[11] 4,115,691
[45] Sep. 19, 1978

[54] APPARATUS FOR IDENTIFYING COMPUTERIZED AXIAL TOMOGRAPHS

[75] Inventor: William Henry Oldendorf, Los Angeles, Calif.

[73] Assignee: EMI Limited, Middlesex, England

[21] Appl. No.: 748,720

[22] Filed: Dec. 8, 1976

[30] Foreign Application Priority Data

Dec. 23, 1975 [GB] United Kingdom ............... 52525/75

[51] Int. Cl.² ...................... G03B 41/16; G03C 9/00; A61B 6/00
[52] U.S. Cl. .............................. 250/312; 250/445 T; 250/476
[58] Field of Search .................. 250/445 T, 476, 312, 250/363 S

[56] References Cited
U.S. PATENT DOCUMENTS

| 3,714,428 | 1/1973 | Gasaway | 250/476 |
| 4,005,527 | 2/1977 | Wilson | 250/312 |

Primary Examiner—Alfred E. Smith
Assistant Examiner—T. N. Grigsby
Attorney, Agent, or Firm—Cooper, Dunham, Clark, Griffin & Moran

[57] ABSTRACT

Radiographic apparatus includes indicium means for indelibly imprinting computerized axial tomographs with identification data which relates to the position of the tomographic slice in relation to a fixed datum position such as the top of a patient's head. The indicium comprises a member having characteristically varying radiopacity which is positioned in the vicinity of the radiographic slice so as to be scanned by the exploring radiation and is fixedly secured in relation to the datum position.

7 Claims, 3 Drawing Figures

APPARATUS FOR IDENTIFYING COMPUTERIZED AXIAL TOMOGRAPHS

The present invention relates to radiography, and it relates more especially to that branch of radiography which is known as computerised axial tomography.

Computerised axial tomographic apparatus, such as that described in U.S. Pat. No. 3,778,614 is capable of utilising penetrating radiation such as X- or γ-radiation to accurately evaluate the absorption (or transmission) coefficient, with respect to the radiation utilised, at each of a plurality of closely spaced locations distributed over a cross-sectional slice through a body under examination. In a typical examination of a body, several adjacent and substantially parallel slices thereof are investigated, and a visual record comprising some form of plot or map of the evaluated coefficients is produced for each slice.

It is desirable that each visual record be clearly identified with the slice of the body to which it relates, in a manner which not only ensures correct correlation of records with slices but also ensures that, should a subsequent re-examination of the patient be called for, the slices investigated during the re-examination can be accurately coincident with the slices examined during the original examination.

It is an object of this invention to provide radiographic apparatus having at least one of the facilities referred to in the immediately preceding paragraph.

According to the invention there is provided radiographic apparatus including source means for projecting penetrating radiation through a slice of a body along a plurality of substantially linear paths, detector means for detecting the radiation emergent from the body along each of said paths and for producing output signals indicative of the absorption suffered by said radiation on traversing said paths, and an indicium member, disposed adjacent said body so as to a traversed by said radiation and formed of or including material which absorbs said radiation to an extent which differs from the absorption of matter surrounding said member, the arrangement being such that said member is characteristic of said slice. Preferably, said indicium member is fixedly located in relation to a particular part of the said body.

In order to irradiate the body along each of the aforementioned paths, it has been found convenient to scan the source and detector means linearly relative to the body, then to rotate the source and detector means through a predetermined angle about an axis perpendicular to the plane of interest and then to scan the source and detector means linearly relative to the body in approximately the opposite direction to the previous linear scan. This procedure of alternate linear scans and predetermined increments of rotation is continued until a total rotation of about 180° or more has been achieved.

Figure 2:
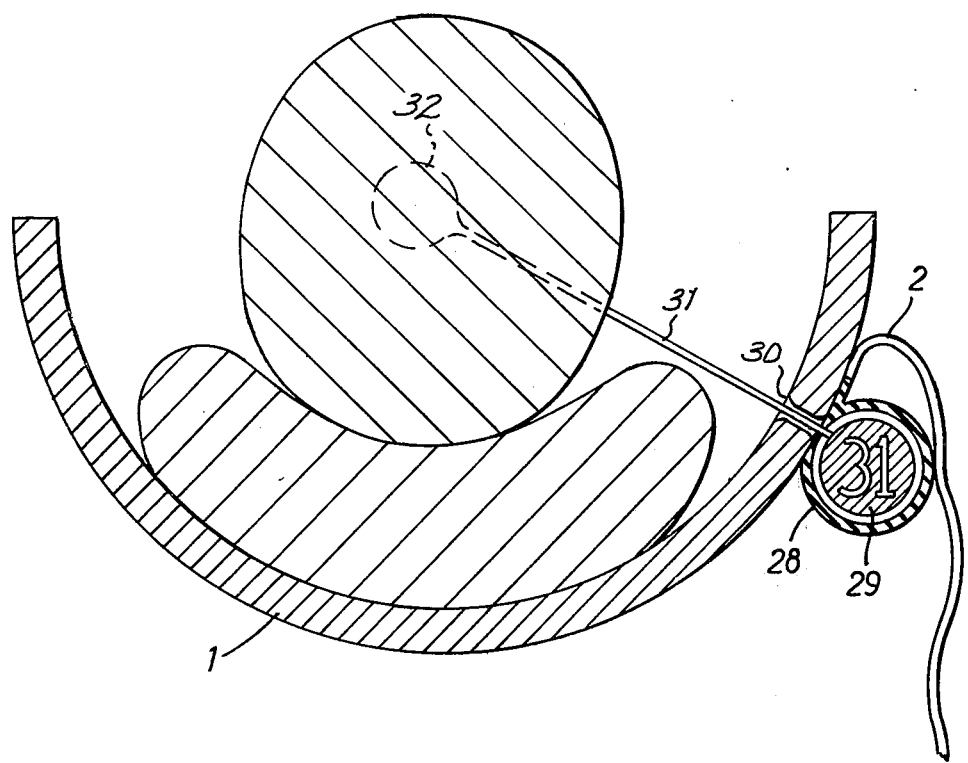
Figure 3:
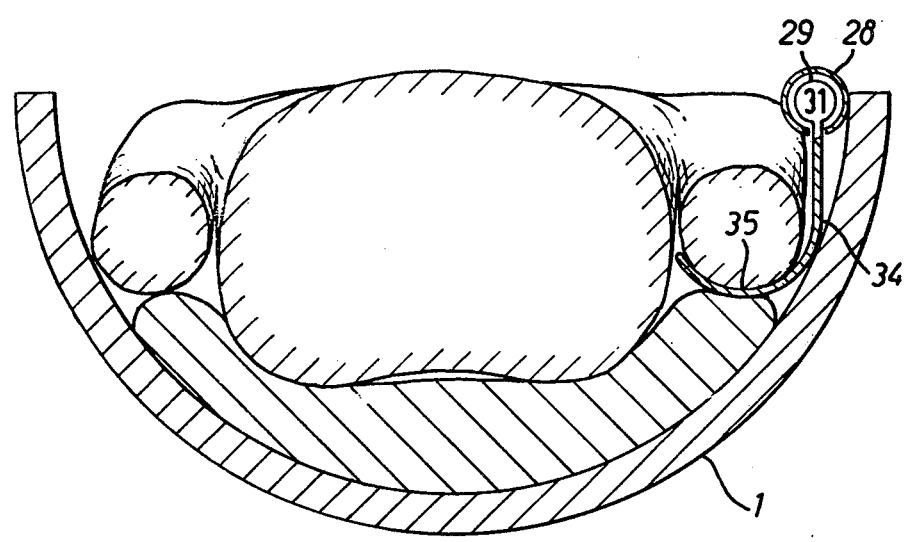

In order that the invention may be clearly understood and readily carried into effect, one embodiment thereof will now be described, by way of example only, with reference to the accompanying drawings of which:

FIG. 1 is a general side elevational view, partly in cross-section, of apparatus in accordance with one example of this invention, FIG. 2 shows, a section on lines II—II of FIG. 1, and FIG. 3 shows a section on lines II—II of FIG. 1 for an alternate form of contact member.

Referring now to FIG. 1 of the drawings, a patient (not shown) to be examined is constrained to lie on a bed 1 with the relevant part of his body disposed so as to be irradiated. In order to restrain the patient, he is secured in the bed 1, which is generally of semi-cylindrical, unitary construction, by means of a strap 2. The bed 1 is slidable relative to a carriage 3 which, in turn, is slidable relative to the main frame 4 of the apparatus, firstly in order to allow the patient to be placed on the bed and secondly to permit the relevant part of the patient's body to be examined. At least the latter function is preferably carried out by means of electric motor means (not shown) and monitored as described in U.S. application Ser. No. 726,051.

A source 5 of a fan-shaped, substantially planar beam of X- radiation, and an associated detector arrangement 6 with associated collimator means 7 are disposed on either side of the bed 1. These components are arranged to execute rotational and translational scans relative to the bed by means of respective electric motors (not shown) which drive shafts 8 and 9 respectively. Shaft 8 drives a pin member 10 which constitutes part of a geneva mechnism for effecting the rotational scan, this scan being carried out in angular steps of a few degrees. In this example, the angle of the fan-shaped beam of radiation is 10°, and the angular steps are each of ten degrees. The detector arrangement 6 contains thirty detectors distributed across the breadth of the beam of radiation, each detector being disposed at $\frac{1}{3}$° to its neighbour. The fan-shaped beam is thus sectioned up into thirty pencil-like portions which irradiate respective paths through the body. The remainder of the geneva mechanism comprises a fixed ring 11, which carries an annular bearing 12 around which a movable, toothed ring 13 can move, such motion of course being perpendicular to the plane of the paper. The ring 13 carries with it, as it rotates, a frame upon which are mounted the components which are used for effecting the translational scan, including the electric motor which drives the shaft 9. This motor is a reciprocating motor.

Shaft 9 drives an endless, toothed rubber belt 14 by means of a toothed drive wheel 15; the belt 14 extending out of the plane of the paper and passing over a toothed idler wheel (not shown). Attached to one run of the belt 14 is a yoke 16, of elongated oval shape in elevation, which carries the X-ray source 5 and the detector/collimator assembly, 6 and 7. The yoke 16 carries a frame 17 bearing rollers such as 18 which run in grooved, linear tracks 19 formed in a member 20 attached to the ring 13. The member 20 thus rotates with ring 13 but does not take part in the translational scan; the yoke 16 being arranged to translate relative to it. Fore-and-aft movement of the yoke 16 (i.e. left-to-right movement in FIG. 1) is restricted by means of a pair of rollers 21 which roll on a plate member 22 which, like the member 20, rotates but does not take part in the translational scanning.

In order to maintain an even distribution of mass despite the fact that the source 5 takes part in the translational scanning a counter-balance weight 23 is secured to the opposite run of belt 14 to the yoke 16 and thus executes lateral scans in the opposite direction to the source 5. The weight 23 runs on a pair of rods 23a, 23b.

The sequence of events is thus that the yoke 16 and its attachments (including the source 5 and the detector arrangement 6) are caused to execute a first lateral scan relative to the bed 1; the ring 13 and its attachments (including the yoke 16) are rotated through an angle of ten degrees relative to the bed 1; the yoke 16 and its attachments then execute a second lateral scan relative to the aperture, this scan being in substantially the opposite direction to the first lateral scan, this being followed by a second rotational step of ring 13 and its attachments, and so-on until the total angular movement of ring 13 is at least 170°.

The source 5, as mentioned previously, is arranged to produce a fan-shaped beam of radiation which extends above and below the plane of the paper, the angle of the fan being, in this example, ten degrees. It will be recalled that the detector arrangement 6 includes thirty radiation sensitive detectors, each responsive to radiation travelling along a respective radial path in the aforementioned beam. Thus, the radiation which can be received by each detector is defined by a respective collimator in the collimator means 7. As a lateral scan proceeds, each detector provides output signals relating to the amount of radiation passed through the body along a plurality of different paths; the width of each path being determined by electrical timing pulses which are produced during each lateral scan and used to control the integration time of integrator circuits (not shown) which are provided for each detector in the detector arrangement 6. The integrators feed processing circuits (not shown) arranged to process the data to provide a representation of the variation, with position across the planar slice of interest through the patient's body, of absorption of the X- radiation from the source 5. Such processing will not be described further herein, since it forms no part of this invention, but examples of suitable processing arrangements can be found in U.S. Pat. No. 3,778,614 and in U.S. Pat. No. 3,924,129 for example.

The aforementioned electrical timing pulses are derived, in this example, by means of a graticule member 25, which comprises a translucent member bearing equally spaced opaque lines, and lamp and photocell detector units 26, 27. The member 25 is mounted, by means of a bracket, to a part of the apparatus which rotates, but does not take part in the translational scanning. The units 26 and 27, which are carried by the yoke 16, thus scan along the graticule member 25 during each lateral scan.

The present invention involves, in this example, disposing a stack of plastic discs, secured together to form a rod, adjacent the body being investigated. Each disc carries a unique indicium and in this example the indicia comprise arabic numerals, The discs are each one centimetre thick, since this corresponds with the maximum thickness of the fan-shaped beam of radiation produced by the source 5. In other circumstances, of course, other thicknesses could be used. The rod, in this example, is slidably mounted in a tubular plastic housing 28 attached to the outside of the bed 1, and this arrangement can be seen more easily from FIG. 2 which represents a section through the bed and its attachments on the arrows II—II of FIG. 1, but on an enlarged scale.

Referring now to FIG. 2, the housing 28 is secured to the bed 1 by any convenient means. The rod is shown at 29 and it can be seen that taking a cross section through the rod 29 at any position along its length exposes the numeral carried by the disc which is intersected by the cross section. In this example, the numeral exposed is '31'. The numerals themselves comprise apertures formed in the plastic material of which the discs are constructed and thus attenuate the radiation less than their surroundings.

The bed 1 is formed, adjacent the end thereof which is to be occupied by the patient's head, with a longitudinal slot 30 which runs through the housing 28 as well. This is to accommodate a transversely extending locating bar 31 which is secured to one end of the rod 29 and can be moved into contact with the top of the patient's head at 32 so as to accurately position all of the indicia relative to a particular part of the body. The rod 29 can be slid longitudinally along the housing 28 by means of an end adjustment screw (not shown) threaded into the end of housing 29 adjacent the patient's head so as to cause said locating bar to contact the patient's head. The adjustment screw is provided with suitable means of known form to lock it in position, once said bar is in contact with the top of the patient's head.

In operation, when a given slice of the body is being examined, the radiation traverses the rod 29 as well as the body. When the reconstruction process is carried out, the absorption coefficients at various locations distributed over a cross sectional slice taken through the rod 29 will be evaluated in the same way, and at the same time as the corresponding coefficients for the relevant planar slice of the body. The reconstruction is, in fact, carried out as if the bed 1 and the rod 29 were part of the body. Because the indicium disposed in the same plane as the slice of the body being examined is also subjected to the exploring radiation, and since the absorption coefficient of said indicium differs from its surroundings, the visual record, produced after the evaluation process has been carried out, will comprise a map of the evaluated absorption coefficients of both the body and the indicium. The record thus indelibly contains an indication of the distance of the irradiated slice of the patient's body from the top of his head. This indication is useful not only to avoid visual records being associated with incorrect slices of the body, but also to permit accurate alignment of the patient should a subsequent re-examination and/or radiotherapy treatment prove necessary.

In order to facilitate re-alignment, it can be desirable to make the tubular housing 28 of transparent plastics material and to print the relevant indicium on the outside edge of each plastic disc of the rod 29 as shown at 33. If then a fine line of light is shone onto the housing 28 in the irradiation plane, the relevant numeral will be strongly illuminated. The rod 28 is first positioned correctly in relation to the patient's head by means of the aforementioned locating bar and the bed 1 is then slid relative to the carriage 3, preferably under the control of an electric motor, until the desired number on the edge of the relevant disc is illuminated. This also ensures that the radiation passes exactly through one disc of the rod 29 and does not straddle two discs, which would cause a confused indicium to be provided on the visual record.

It will be appreciated that, in the foregoing embodiment of the invention, it is necessary to extend the region over which the absorption coefficients are evaluated outside the region in which the body is located. This can be undesirable in some circumstances as it gives rise to extra processing and possibly also the necessity of increasing the amplitude of the lateral scans. One way of overcoming this problem is shown in FIG. 3. The rod 29 is formed as a crutch 34 which is located inside the bed 1 and slides relative thereto so as to contact the underarm of the patient, as shown at 35.

This is thus used, instead of the top of the head, as the point of reference. In this case the rod 29 lies beside the patient in the bed 1 and takes advantage of the fact that the bed has to be wide enough to accommodate the patient's shoulders so that in general, once below the shoulders, there is sufficient space between the patient and the bed to accommodate the rod 29.

The apparatus shown and described may be modified without departing from the scope of the invention. For example attenuator blocks may be placed between the source and the bed and between the bed and the detector arrangement for tending to equalise the absorption suffered by the radiation on traversing paths of different lengths through the body. Such attenuators would, of course, rotate with the source and detector arrangement.

What I claim is:

1. Radiographic apparatus including: source means for projecting penetrating radiation through a slice of the body of a patient along a plurality of substantially linear paths; detector means for detecting the radiation emergent from the body along each of said paths and for producing output signals indicative of the absorption suffered by said radiation on traversing said paths; a stack of similar indicium members disposed adjacent said body, each of which is formed of or includes material which absorbs said radiation to an extent which differs from the absorption of matter surrounding the member, said members being secured together to form a rod; and a contact member associated with said rod and disposed to contact the under-arm of said patient and thereby to cause one of said indicium members to intercept said radiation and thereby be associated with said slice.

2. Radiographic apparatus including: source means for projecting penetrating radiation through a slice of a body along a plurality of substantially linear paths; detector means for detecting the radiation emergent from the body along each of said paths and for producing output signals indicative of the absorption suffered by said radiation on traversing said paths; a stack of plastic discs secured together to form a rod disposed adjacent said body so as to intercept said radiation, each disc bearing a respective identification mark, formed of or inluding material which absorbs said radiation to an extent which differs from the absorption of matter surrounding said mark, to form an indicium member; and a contact member associated with said rod to contact with a particular part of said body and thereby associate one of said indicium members with said slice.

3. Apparatus according to claim 2 wherein each said mark comprises an aperture in said plastics material.

4. Radiographic apparatus comprising means defining a patient position, a source of X-radiation, disposed to irradiate a region of said patient position, indicator means, disposed at said patient position, and bearing a plurality of indicia having different effects on said radiation, each indicium being associated with a respective cross-sectional slice of the body of a patient disposed at said patient position, scanning means for causing said source to move relative to said patient position so as to irradiate said region from a plurality of different positions, and detector means for detecting the radiation emergent from said patient position along at least one beam path for each of said positions, said indicia being disposed so that throughout said relative movement radiation travelling from the source to the detector means, to examine a cross-sectional slice of the body, is substantially only intercepted by the indicium associated with that slice.

5. Radiographic apparatus including: source means for projecting penetrating radiation through a slice of the body of a patient along a plurality of substantially linear paths; detector means for detecting the radiation emergent from the body along each of said paths and for producing output signals indicative of the absorption suffered by said radiation on traversing said paths; a stack of similar indicium members, each of which is formed of or includes material which absorbs said radiation to an extent which differs from the absorption of matter surrounding the member, said members being secured together to form a rod; a bed supporting said body; a tubular housing, also supported by said bed and disposed longitudinally thereof, said rod being inserted into said housing and being capable of sliding motion therein in said longitudinal direction; and means for causing one of said members to intercept said radiation and thereby be associated with said slice.

6. Apparatus according to claim 5 wherein said contact member comprises a bar transversely extensive from said rod, and said bed and said housing are formed with juxtaposed longitudinal slots through which said bar can protrude inwardly of said bed, said bar being disposed to contact the top of the head of a human patient.

7. Apparatus according to claim 5 wherein each disc is imprinted on its edge with a replica of its respective indicium and said housing is formed of optically transparent material enabling said replica to be read visually therethrough.

* * * * *